United States Patent
Yoshimine et al.

(10) Patent No.: US 7,045,931 B2
(45) Date of Patent: May 16, 2006

(54) CHIP QUARTZ OSCILLATOR AND LIQUID-PHASE SENSOR

(75) Inventors: Hiroshi Yoshimine, Motono-mura (JP); Hiroyuki Sota, Saitama (JP)

(73) Assignees: Amersham Biosciences KK, Tokyo (JP); Yoshio Okahata, Kanagawa (JP)

( * ) Notice: Subject to any disclaimer, the term of this patent is extended or adjusted under 35 U.S.C. 154(b) by 152 days.

(21) Appl. No.: 10/432,414

(22) PCT Filed: Dec. 7, 2001

(86) PCT No.: PCT/JP01/10745

§ 371 (c)(1),
(2), (4) Date: Oct. 1, 2003

(87) PCT Pub. No.: WO02/47246

PCT Pub. Date: Jun. 13, 2002

(65) Prior Publication Data

US 2004/0051595 A1 Mar. 18, 2004

(30) Foreign Application Priority Data

Dec. 7, 2000 (SE) .............................. 0004547

(51) Int. Cl.
*H01L 41/08* (2006.01)

(52) U.S. Cl. .................. 310/322; 310/324; 310/345
(58) Field of Classification Search ............. 310/312, 310/321, 322, 324, 345
See application file for complete search history.

(56) References Cited

U.S. PATENT DOCUMENTS

| | | | | |
|---|---|---|---|---|
| 3,937,991 A | * | 2/1976 | Massa et al. ............... | 310/324 |
| 4,176,524 A | * | 12/1979 | Kamiyama et al. ........... | 62/140 |
| 4,368,400 A | * | 1/1983 | Taniguchi et al. .......... | 310/322 |
| 4,789,804 A | * | 12/1988 | Karube et al. ............. | 310/311 |
| 5,021,701 A | * | 6/1991 | Takahashi et al. .......... | 310/345 |
| 5,455,475 A | * | 10/1995 | Josse et al. ............. | 310/316.01 |
| 5,925,972 A | * | 7/1999 | Shrader et al. ............ | 310/338 |
| 6,472,798 B1 | * | 10/2002 | Kishimoto .................. | 310/344 |

FOREIGN PATENT DOCUMENTS

| | | |
|---|---|---|
| JP | 62-044525 | 3/1987 |
| JP | 63-266338 | 11/1988 |
| JP | 01-204508 | 8/1989 |
| JP | 05-021476 | 3/1993 |
| JP | 07-058575 | 3/1995 |
| JP | 2759659 | 3/1998 |
| JP | 2759683 | 3/1998 |
| JP | 2759684 | 3/1998 |
| JP | 2001-153777 | 6/2001 |

* cited by examiner

*Primary Examiner*—Mark Budd
(74) *Attorney, Agent, or Firm*—Royal N. Ronning, Jr.; Yonggang Ji (57) ABSTRACT

The present invention relates to a chip quartz oscillator. In an embodiment of a chip quartz oscillator S in accordance with the present invention, a quartz oscillator 2, which has a detection electrode 3 on a surface thereof and a non-detection electrode on the other surface thereof, is fixed on a substrate 1, and each of the electrodes is connected electrically to a terminal 4 or 4' on the substrate 1. While keeping the non-detection electrode in contact with the substrate 1, the quartz oscillator 2 is fixed on the substrate 1, by flexibly bonding the side-wall 2''' of the quartz oscillator 2 along its circumference to the surface of the substrate 1 by using the elastic bonding agent 5. Thus, the oscillation surface of the quartz oscillator 2 is supported distributively on the substrate 1 in a surface-contacting and non-adhesive manner.

2 Claims, 8 Drawing Sheets

CHIP QUARTZ OSCILLATOR AND LIQUID-PHASE SENSOR

TECHNICAL FIELD OF INDUSTRIAL APPLICATION

The present invention relates to a quartz oscillator sensor and an oscillation circuit for a liquid-phase sensor in which an elastic wave element such as quartz oscillator is used as a detector immersed in a liquid medium.

PRIOR ART

Piezoelectric acoustic wave devices such as quartz oscillator can be utilised as mass sensors on the basis of the principle that a material adsorbed on the electrode surface changes the fundamental oscillation frequency of the oscillator in proportion to the mass of the adsorbate; the change has been proven experimentally to conform to the theoretical formula proposed by Sauerbrey (Sauerbrey, G., Z. phys. 155 (1959), p. 206–222). Owing to the high detection sensitivity predicted by the formula, a micro-measurement method using such a sensor is far superior to general mass measurement methods using mechanical balances, and thus the method has been put into practical use, for example, in quantitative measurement of odorous molecules or aerosols in the gaseous phase.

A quartz oscillator is generally a circular or rectangular crystalline plate shaped by cutting along a particular crystal face for a natural characteristic oscillation of the crystal and is provided with electrodes made of thin layers of vapour-deposited metal. Depending upon its cutting angle, each crystal plate is designated as an AT, BT, CT, X, or Y cut. The quartz plate is situated between a pair of thin-layer metal electrodes placed symmetrically in parallel. An induction electrical field between the electrodes results in distortion in the quartz crystal, whereas a distortion produces an electrical charge; the so-called piezo-electrical phenomenon achieves the reversible and steady oscillation.

Usually, the surface area of the quartz plate is wider than that of the electrode. The non-electrode area without the piezo-electrical effect on the quartz plate helps to propagate the elastic wave occurred at the electrode area while moderately attenuating the wave. Thus, it is an area that is responsible for the so-called "confinement effect." Thus, in designing quartz oscillators, the selection of shape and size of the quartz plate is most important in order to reduce unfavourable sub-oscillations such as spurious oscillations caused by adverse effects such as end-face reflection of the plate, etc.

A means of mechanical fixation is necessary for mounting such a quartz oscillator for use as a sensor. A quartz oscillator element for use as an electronic component used in the gaseous phase is usually designed to be supported by a minute contact area of the quartz plate end face by using a supporting metal lead in order to lower the stress as far as possible in both the directions of the radius and the thickness of the quartz plate. In other words, the elastic wave is attenuated in the vicinity of the end face and the influence of the mounting forces is small; the contact area is taken into consideration to reduce the area as much as possible so as not to impose the mounting forces on the quartz plate.

The first liquid-phase elastic wave element sensor was reported by Basstiaans and his colleague in 1980 (Konash, P. L. and Bastiaans, G. J., Anal. Chem. 52 (1980), p. 1929–1931). Ever since the first report, many studies have been reported on elastic wave element sensors operating in the liquid phase; the technology is expected to be applicable to detect substances, as targets under test, including pharmaceutical agents usually dissolved in the liquid phase, and chemical substances such as agricultural pesticides and food additives, as well as bio-functional molecules represented by nucleic acids such as DNA and RNA, and proteins such as antibodies, hormone receptors, and lectins, which function only in the liquid phase.

However, a problem occurs when the quartz oscillator, which is an electrical element originally designed on the assumption of using it in a gaseous phase, is used as a sensor in a conducting solution—namely an electrical short-circuit occurs between the electrodes in solution. In all the previous studies, without exception, it has been necessary to take measures to prevent this short-circuit. Specifically, in a liquid-phase quartz oscillator sensor, the one of the pair of electrodes which acts as a detection surface is exposed to the liquid phase, while the other electrode is protected in some way against coming into contact with the solution. Of course as the quartz oscillator is an element which is based on the principle of a constant stable elastic oscillation, any mechanical constructions to prevent the electrode from coming into contact with the solution, which interfere with the oscillation of the quartz oscillator, should be definitely avoided.

The high-quality frequency stability of a quartz oscillator as an elastic wave element is represented by a high Q (quality factor). The Q markedly decreases as the degree of interference with the oscillation of the quartz oscillator increases. In addition, in the liquid-phase sensor, in which the quartz plate is exposed to a liquid with a high viscosity as compared with gas, being in contact with liquid itself may have an interfering effect and, as a consequence, the Q may decrease greatly; the Q may also decrease to the minimum due to an improper mechanical construction. In other words, in the worst case the oscillation might stop.

Figure 14:
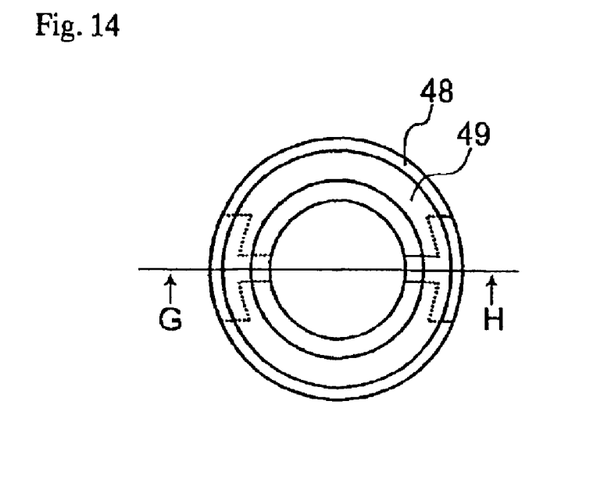
FIG. 14 is a schematic illustration showing the prior art method for supporting a circular quartz oscillator with O-rings.
Figure 15:
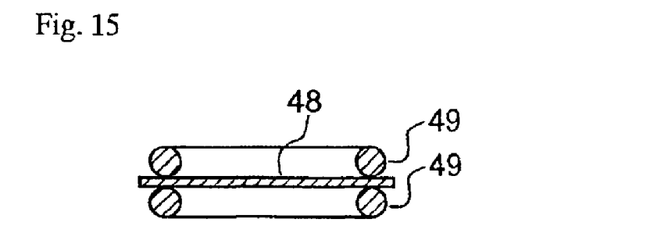
FIG. 15 is a sectional view along the line G–H indicated in FIG. 14.
Figure 16:
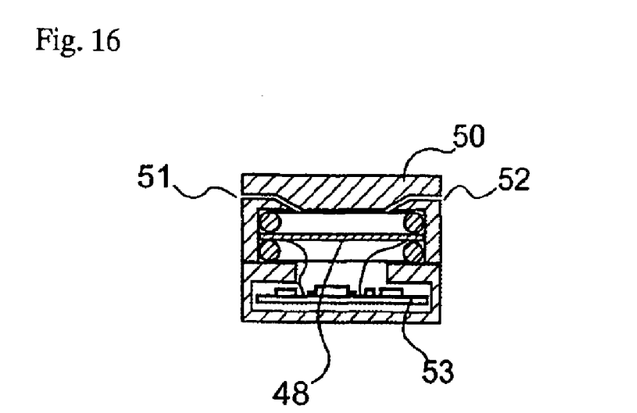
FIG. 16 is a sectional view of the flow-type liquid-phase quartz oscillator sensor in which the chip quartz oscillator indicated in FIG. 14 is installed.

For example, there is a method, as frequently found in study reports on the development of devices with quartz oscillators (for example, Masson. M. et al., Anal. Chem. 67 (1995), p. 2212–2215, U.S. Pat. No. 5,135,852, etc.), by which one of a pair of electrodes alone is allowed to come in contact with liquid; a circular quartz oscillator is fixed with a pair of rubber O-rings or gaskets placed on both sides thereof. FIGS. 14 and 15 show the positional relationship between the quartz plate and the O-ring in a quartz oscillator sensor in typical prior art example. FIG. 14 is a plan view from above, and FIG. 15 is a sectional view along line G-H in FIG. 14. In these figures, the quartz oscillator 48, which is circular in shape and has a pair of electrodes in both sides thereof, is placed between a pair of O-rings or gaskets 49, and installed in the flow-type liquid-phase quartz oscillator sensor 50 as indicated in FIG. 16. FIG. 16 contains an inflow entrance 51, a drain hole 52, and a circuit board 53.

In FIGS. 14–16, the O-rings or gaskets 49 act to prevent the solution flowing into the cavity where the non-detecting electrode is present, as well as to fix the quartz oscillator to the inside wall of the measurement cell containing the solution. In this method employed in the previous example, a mounting point is chosen on a surface of the quartz plate in the vicinity of its end face where the oscillation is hardly interfered with and the quartz plate is fixed via the elastic rubber, resulting in secure protection against leaks and a flexible mounting. However, the adjustment of the tightening pressure for the O-ring or gasket 49 is so delicate that reproducibility is unable to be expected. Furthermore, the quartz plate itself is handled directly when it is being placed between the O-rings or gaskets 49 in a narrow flowcell, and therefore, there is a risk of damaging the fragile quartz plate. Even when fixed firmly, the quartz oscillator might be distorted due to pressure fluctuations in the solution being tested. These act on the quartz plate, and because there is usually a cavity on the side of non-detection electrode of the quartz plate, deflect the middle of the quartz plate towards and away from the cavity. Moreover, in the case of the infinitesimal deformations of the vessel caused by temperature changes or hydraulic pressure changes, the quartz plate is directly stressed by such deformations. In any event, such deformations of the quartz oscillator resulted in a marked decrease in the Q and an unsteady oscillation in the liquid-phase sensor; many examples have shown that the oscillation halts in the worst case.

For example, Japanese Patents No. 2759659, No. 2759683 and No. 2759684 disclose applications in a liquid-phase sensor of a quartz oscillator with a barrier on one side covered with elastic and plastic materials. In this example, the quartz plate is hardly subjected to the mounting forces in the structure, because the covering is fixed adhesively at the contact positions similar to those of the above-mentioned O-ring and the quartz oscillator. However, a relatively large amount of sample solution is required for the measurement, even when it is possible to immerse such a bulky structure (i.e. the quartz oscillator with the covering) in the sample solution. This, as a matter of course, limits the range of objects testable by the liquid-phase sensor; it is unsuitable for measurements in which only a small amount of sample is available for the detection of substances including the above-mentioned bio-functional molecules. Changing the sensor to a flow-type sensor effectively improves the apparent desensitisation due to an apparent increase in amount of sample solution, thereby markedly reducing the actual amount of sample solution required. However, it is difficult to install the quartz oscillator with the components as disclosed in the above-mentioned patent into a flow cell, and even if it were possible, further efforts are required to design the device in which a quartz oscillator itself is not subjected to deformation forces from the fixation vessel.

The theoretical sensitivity of the liquid-phase quartz oscillator sensor is defined uniquely according to the above-described Sauerbrey's formula, where the fundamental oscillation frequency and the area of the electrode are variables. However, the practical effective sensitivity of a liquid-phase quartz oscillator sensor, although defined based on the theoretical sensitivity, depends on the normal response to an increase in mass on the electrode of the quartz oscillator, or it depends on how the minimal change of time changes (decrease) in signal frequency can be detected as a significant change. In other words, the above-mentioned effective sensitivity largely depends on the existence and the degree of influence of insignificant signals such as noises and drifts, which mask small time changes in signal frequency.

As described above, when a quartz oscillator is placed in a solution, the energy dissipation rate is elevated and effective impedance increases; the Q decreases greatly when compared with the quartz oscillator placed in a gas phase. This property is inevitable for the application. This means impairment of the frequency maintenance ability or the high buffer action, which is an original property of the quartz oscillator, against the change of electrical load of applied voltage, etc. or against the change of mechanical load resulted from the change in the physical properties (pressure, viscosity, etc.) of solution in contact with the device. As compared with the quartz oscillator placed in a gas phase, a sensor operating in a liquid phase displays a lot of noise and/or large drifts, because its output signal changes easily according to the load fluctuations as described above. Thus, when usual quartz oscillator circuits, which had been developed on the assumption that the oscillation occurs in a gas phase, were used in liquid-phase sensors without any modification, steady oscillation was often impossible to achieve.

Moreover, since the liquid-phase quartz oscillator sensor is often used as a chemical sensor or a biosensor, the sample solution is usually an electrically conducting fluid that contains electrolytes; thus its detection electrode is always exposed to such an electrically conducting fluid. This has been recognised by persons who have developed liquid-phase quartz oscillator sensors, and several measures to solve the problem have been proposed by them. In addition, sensors with higher sensitivity and higher-throughput performance have been demanded owing to the recent advancement of technology of molecular biology and analytical chemistry. Device multiplexing in a sensor has made simultaneous multi-measurement commonplace. The device-multiplexing trend requires measures against another type of short-circuit besides the above-mentioned problem of short circuit between a pair of electrodes in a single quartz oscillator in the oscillation circuit system that drives the sensor. Specifically, it is necessary to deal with the problem of short-circuit caused by a common electrical ground shared by the oscillation circuits corresponding to the respective electrodes when multiple electrodes are simultaneously immersed into a conducting solution.

For example, Unexamined Published Japanese Patent Application (JP-A) No. Hei 11-163633 has disclosed the example of obtaining the amplification degree required for the quartz oscillation in a liquid by connecting three inverters in series to an amplifier circuit. This example is based on designing energy compensation for the loss of energy dissipated into the liquid phase by that gained by the amplification. Similarly designed circuits have also been proposed in a report of Barnes and his colleague (Barnes, C., Sens. Actuators A., 29 (1991), p. 59–69) and U.S. Pat. No. 4,788,466. These publicly known technologies can be assumed as an effective strategy when the energy is dissipated markedly, and thus, the quartz oscillator halts, but the Q of quartz oscillator is not improved based on the strategy. Because of this, it is ineffective for noises from the concomitant devices, for example, noise directly transmitted from the DC power source unit for rectification and voltage drop down of the power from the AC line or transmitted from output-signal processing systems as well as fluctuations of applied power voltage due to radiation noise around the quartz oscillator. Thus, improvement of the effective sensitivity cannot be achieved by these methods. In addition, device multiplexing, specifically, the arrangement of multiple oscillation circuits in a single device unit has not been assumed in the above-mentioned disclosed technologies.

An example of circuit using a battery and photocoupler has been proposed in a report of Bruckenstein and his colleague (Bruckenstein, S. and Shay, M., Electrochimica Acta, 30 (1985) p. 1295–1300). However, this example is not designed for device multiplexing, and the signals from a pair of differentially operating quartz oscillator sensors, of which one is for sample measurement and the other is for reference measurement, are connected directly inside the closed circuit. Thus, there is the problem of short-circuits between the oscillation circuits that occur as the pair of quartz oscillator sensors is immersed into the same solution. Further, an example of circuit, using a battery as a power source and having a transformer inserted in its signal system, has been proposed in U.S. Pat. No. 3,561,253. In this example of circuit, the insulation is achieved by using the transformer, and therefore, it has a small effect on the noises from external signal processing system or the influences of load fluctuation, but it cannot remove the elements of alternating noise such as high frequency noise, etc.

Problems to be Solved by the Invention

As described above, when an elastic wave element such as a quartz oscillator is used as a liquid-phase sensor, oscillation with a low Q (for example, a Q of 2000 or less as compared to Qs of up to 100000 which can be achieved for quartz oscillators used in the gaseous-phase) should be expected because mechanical load increases by contact with liquid, which is inevitable for the application. To achieve high performance, multi-functionality and high reliability of sensors which are forced to operate under the condition of a low Q, it is necessary to design the electrical and physical configuration by taking into consideration the following points: (1) further decreases in Q should be avoided by keeping the mechanical stress load on the oscillator, which results from the mounting of the oscillator in the cell, to a minimum; (2) unfavourable external load variations should not be passed to the quartz oscillator without autonomous buffering capacity (tolerance to the load fluctuation) required for outputting the stable signal frequency. In other words, in order to ensure a stable oscillation frequency from the quartz oscillator, the voltage supplied to the oscillator must be constant as even a change of less than 1 mV in the DC voltage of, for example 5V, applied to the oscillator results in a significant loss of frequency stability. Therefore, the power supply to the quartz oscillator should be arrange such that voltage is constant to an accuracy of 1 mV or better, no matter what happens in order to prevent input voltage-dependent, undesirable frequency changes; and (3) noise should not be transmitted in. In addition to these, in this configuration, not only should insulation should be ensured between the electrodes on a single quartz oscillator but also the requirement of electrical isolation of each oscillation system should be satisfied by preventing short circuits between the electrodes through the solution, or short circuits between conducting materials in contact with a liquid and other devices through a common electrical ground or static connection when multiple quartz oscillators are present. It has been a problem to meet these conditions in the prior art and the purpose of the invention is to provide a quartz oscillator which overcomes some or all of these problems.

DISCLOSURE OF THE INVENTION

In the present application of the invention, a new design is presented which attempts to overcome these problems that were unsolved by the prior art.

Thus an object of the present invention is to provide a chip quartz oscillator in which the quartz oscillator is prevented from being distorted by external deformation forces.

A further object of the present invention is to provide a combined quartz oscillator element, in which multiple chip quartz oscillators can be arranged on a common mounting substrate.

Another object of the invention is to provide chip quartz oscillators in which the provision of a flexible mounting is provided by means which can easily accommodate variations in size of the quartz oscillators.

A further object of the present invention is to provide chip quartz oscillators in which the quartz oscillator mounting forces are spread evenly over the circumference of the quartz oscillator.

An additional object of the present invention is to provide chip quartz oscillators in which liquid is prevented from coming into contact with the non-detection electrode of the quartz oscillator.

Another object of the present invention is to provide chip quartz oscillators in which the quartz oscillator is supported by a substrate without the oscillation of the quartz oscillator being affected by the substrate.

An additional object of the present invention is to provide chip quartz oscillators in which the quartz oscillator oscillation is not degraded by the stiffness of the mounting mean.

Yet a further object of the present invention is to provide a batch-type liquid-phase quartz oscillator sensor in which a steady oscillation is achieved and unaffected by the pressure fluctuation of the solution.

Another object of the present invention is to provide a flow-type liquid-phase quartz oscillator sensor, in which an unfavourable pressure exerted by mounting is not applied to the fixed quartz oscillator and in which insulation is ensured between the electrodes of quartz oscillator; which sensor has a detection cell for liquid to be tested and works with only the detection electrode on the quartz oscillator surface immersed in a flowing liquid; and in which steady oscillation is achieved and unaffected by the pressure fluctuation of the solution caused by flow rate fluctuation.

Yet another object of the present invention is to provide a quartz oscillator device, with means for preventing the fluctuation of oscillation frequency resulted from the variation of power source voltage caused by external noises and achieving a steady oscillation; and which helps to improve the effective sensitivity of a liquid-phase sensor.

A further object of the present invention is to provide a method for making quartz oscillator devices in accordance with the present invention.

The present invention will be illustrated below by means of examples of embodiments of the invention and drawings.

DETAILED DESCRIPTION OF THE PRESENT INVENTION

Several embodiments of the present invention will be described below in detail with reference to the drawings. However, it is to be understood that the present invention is not intended to be limited to the specific embodiments but covers all variations and modifications covered by the appended claims. It should be assumed that same reference numeral or symbol designates the same or a similar component in the drawings.

Figure 1:
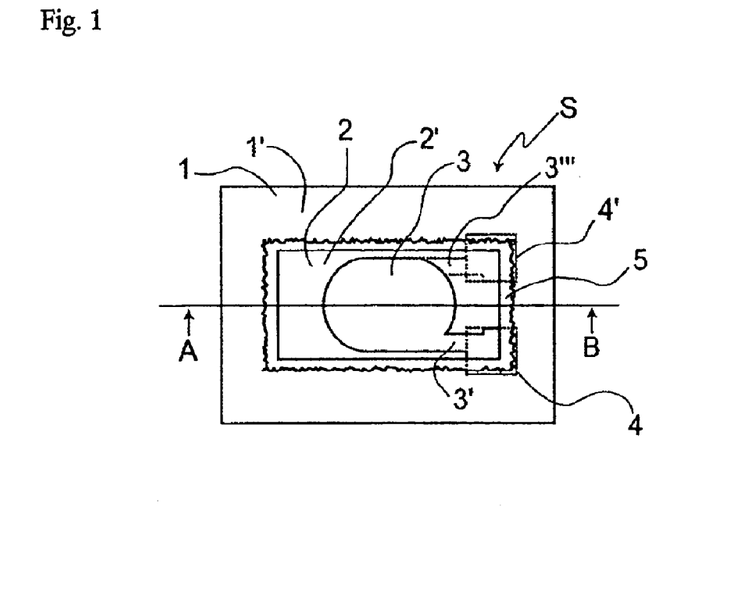
FIG. 1 is a plan view from above schematically showing a first embodiment of a chip quartz oscillator in accordance with the present invention.
Figure 2:
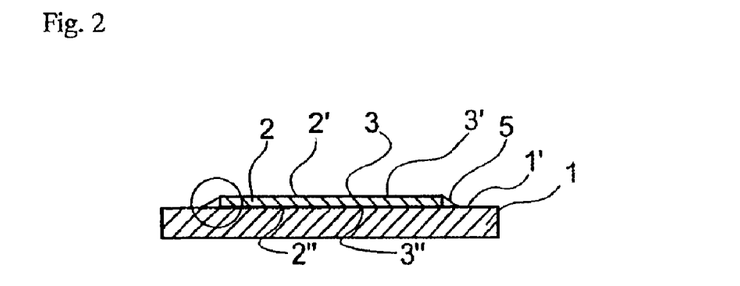
FIG. 2 is a sectional view along the line A–B in FIG. 1.

FIG. 1 is a plan view from above schematically showing the first embodiment of the chip quartz oscillator of the present invention, and FIG. 2 is a sectional view along the line A–B indicated in FIG. 1. In these figures, the chip quartz oscillator S has a rectangular quartz oscillator 2 placed on the upper surface 1' of a substrate 1. Substrate 1 is made of any material which is rigid, non-conducting or able to retain a non-conducting coating, non-soluble in the liquids being tested and preferably inexpensive and easy to work with. Many engineering plastics, metals and ceramics are suitable for this use, in particular the types used for making circuit boards. The quartz oscillator 2 has a detection electrode 3 on a first surface 2' and a non-detection electrode 3" on the opposite second surface 2" i.e. in this case the side facing towards the upper surface 1' of the substrate 1. In an example of an embodiment of the present invention the quartz oscillator 2 is in the order of 4 mm long, 1.6 mm wide and 60 µm thick, other dimensions and shapes are of course possible. Thus the first and second surfaces have an area of 6.4 mm² and the side-wall 2''' of the oscillator is 60 µm deep.

In order to make an electrical connection to the corresponding portion of the substrate 1, a lead electrode 3' (also called a partial electrode) made of a thin metal layer, is connected to the detection electrode 3. The lead electrode 3' extends across the surface of the quartz oscillator to its edge, over the edge and down the side of the quartz oscillator 2 and around the bottom edge of the side-wall to the underside of the quartz oscillator where it is connected, preferably by using a small amount of an electrically conducting bonding agent (not shown), to a first terminal 4 preferably made of a thin metal layer on the substrate 2. Similarly, the non-detection electrode 3" on the opposite surface of the quartz oscillator 2 is electrically connected by a lead electrode 3''' to a second terminal 4' on the upper surface of substrate 1, again preferably by using an electrically conducting bonding agent (not shown). Each of the terminals 4 and 4' is electrically connected to an external terminal placed on the back of the substrate 2 (i.e., on the surface opposite to the one with the quartz oscillator 2) by using an electrical connection such as a via through the substrate 2. With this configuration, a voltage can be applied to the detection electrode 3 and the non-detection electrode 3" from the opposite surface of the substrate 1 to that where the quartz oscillator 2 is placed.

Figure 3:
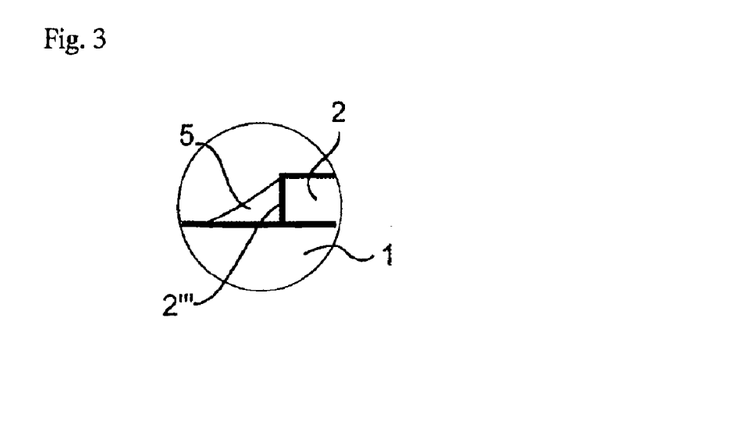
FIG. 3 is an enlarged view of the circled part of FIG. 2.

In order to prevent a short circuit between the detection electrode 3 and the non-detection electrode 3" caused by an electrically conducting fluid coming in contact with the non-detection electrode placed on the back of the quartz oscillator 2, the side-wall 2''' of the quartz oscillator 2 is flexibly fixed and sealed along the whole of its circumference to the substrate 1 by using an elastic bonding agent 5. This bonding agent is preferably not soluble in the liquids being tested and can be, for example, a silicon-resin bonding agent. It should preferably be mobile enough, when it is being applied to the chip, to spread easily while being viscous enough to not penetrate into the contact area between the oscillator and support. After being cured, it should also be elastic enough to allow the oscillator's stabilised motion but it should no longer be mobile. As shown in FIG. 3, which is an enlarged view of the circled part of FIG. 2, the elastic bonding agent 5 is used to fix the side-wall 2''' of the quartz oscillator 2 to the substrate 1; the minimal possible amount of the bonding agent is used in order to keep both top surface (the surface with the detection electrode 3) and bottom surface (the surface with the non-detection electrode 3") of the quartz oscillator 2 free from the bonding agent as this would otherwise adversely affect the performance of the quartz oscillator.

In the chip quartz oscillator S with this configuration, because of the flexible attachment of the quartz oscillator 2 to the substrate 1 by an elastic bonding agent, it is possible to minimise resistance forces due to the attachment to the substrate 1 and to keep the decrease in Q to a minimum for a bulk-wave-mode thickness shear vibration in an AT-cut quartz oscillator or the like. Further, once the quartz oscillator 2 is fixed to the substrate 1, i.e. once the bonding agent has cured, the attachment does not undergo any changes when the chip is mounted in a device as the substrate absorbs all the mounting forces, and therefore no mounting forces are applied to the oscillator chip. This gives the advantage that the state of oscillation is highly reproducible when used repeatedly, a significant advantage when compared to a prior art quartz oscillator fixed by the previous method of mechanical tightening with O-rings or gaskets.

As described earlier, in a previous liquid-phase sensor, a gaseous cavity has been often placed on the back of a quartz oscillator and the quartz plate has been supported at end points thereof, and therefore, there has been the disadvantage that the plate is distorted due to variations in the fluid pressure of a sample solution. This causes the Q to decrease markedly depending upon the pressure and, as a result, the oscillation becomes unsteady or halts. However, in the present invention, the steady oscillation can be maintained as the distortion of the quartz oscillator 2 is prevented, because the oscillation surface, facing the substrate 1, of the quartz oscillator 2 is supported non-adhesively but distributively in contact with the surface of the substrate 1. This is a great advantage over the prior art quartz oscillator, which is sensitive to flow rate changes, is substantially unusable under conditions of medium or high flow rate that causes large pressure fluctuations because of pulses in the flow of liquid, and also tends to limit the use of reciprocating pumps which produce highly pulsating flows. However, these problems can be substantially avoided with the chip quartz oscillator S of the present invention.

The above-mentioned term "non-adhesively" means that the surface of the quartz oscillator facing the substrate 1 is not bonded to the substrate 1 nor is it intentionally kept lifted apart from the substrate; therefore, the back surface can freely oscillate transversely. "Distributively" means that the mounting forces are distributed over the contact area between the substrate 1 and quartz oscillator, preferably distributed evenly over the contact area.

Additionally, in a chip quartz oscillator S of the present invention, it is possible to keep the detection electrode 3 and the non-detection electrode isolated electrically from each other even in a conducting sample solution, because the quartz oscillator 2 is sealingly bonded along its circumference to the substrate 1 by the waterproof elastic bonding agent 5. Furthermore, in the prior art it was necessary to attach a wire directly to the surface electrode of the quartz oscillator during installation. However, in the present invention, the chip quartz oscillator S is an easily replaceable unit because an external electrical connection for the upper electrode can be arranged on the bottom surface of the substrate 1 along with the connection for the lower electrode, thereby advantageously achieving simple installation. In the present invention, there is another advantage that the fragile quartz oscillator can be protected against mechanical damages since the chip quartz oscillator can be handled or replaced on a chip-unit (i.e. chip and substrate) basis, i.e. contact with the fragile chip can be avoided.

A method for manufacturing a chip quartz oscillator in accordance with the present invention can comprise the following steps:

detection and non-detection electrodes and lead electrodes are vapour deposited onto a quartz oscillator;

a substrate having a suitable shape and size is provided with electrodes on the surface which is intended to face the quartz oscillator and through holes from these electrodes leading to the opposite side of the substrate;

conductors leading from the electrodes on the surface of the substrate are provided in the through holes;

conducting bonding compound is applied to the electrodes on the substrate and the quartz oscillator is placed on the substrate with its lead electrodes in contact with the conducting bonding compound;

the conducting bonding compound is cured;

a flexible when cured bonding compound is applied, for example manually by means of a thin pin while viewing with a microscope, or automatically by a robot, around the circumference of the quartz oscillator to bond the side wall of the quartz oscillator to the surface of the substrate; and any excess bonding compound on the upper surface of the quartz oscillator is removed.

Figure 4:
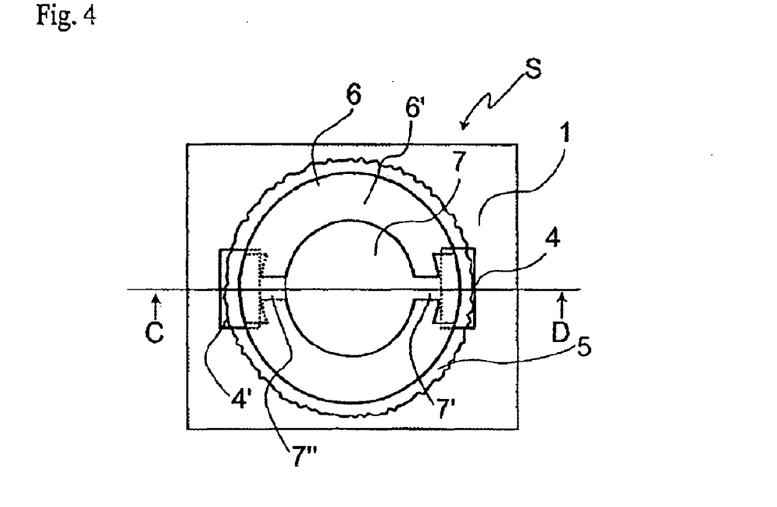
FIG. 4 is a plan view from above schematically showing a second embodiment of a chip quartz oscillator in accordance with the present invention.
Figure 5:
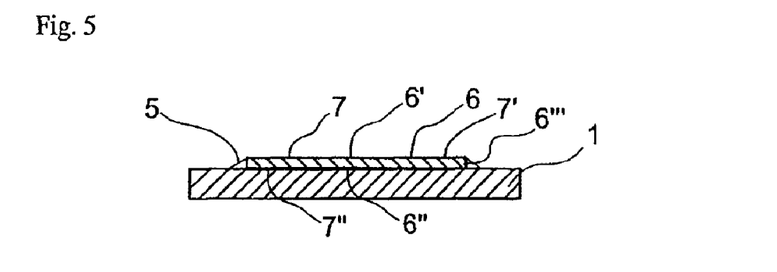
FIG. 5 is a sectional view along the line C–D indicated in FIG. 4.

The above is an example of a rectangular quartz oscillator 2, but a chip quartz oscillator S, in accordance with the present invention, can also be achieved by using quartz oscillators having other shapes. FIG. 4 is a plan view from above schematically showing a second embodiment of a chip quartz oscillator of the present invention, and FIG. 5 is a sectional view along the line C–D indicated in FIG. 4. In a chip quartz oscillator S of this second embodiment, a circular quartz oscillator 6 is arranged on the substrate 1. The quartz oscillator 6, for example, has a circular detection electrode 7 on the first surface 6' opposite to the substrate 1.

A lead electrode 7' made of a thin layer of vapour-deposited metal is wired from an appropriate portion of the detection electrode 7, extends in the direction of the radius of the quartz oscillator 6 on the surface 6' thereof, goes down the side-wall 6''' of the quartz oscillator 6, and extends around to the back surface 6" which faces the substrate 1. The back portion of the lead electrode 7' of the quartz oscillator 6 is electrically connected to the terminal 4 on the substrate 1, preferably using a minimum area and thickness compatible with a reliable connection, by using an electrically conducting bonding agent (not shown). Likewise, a non-detection electrode 7" on the other surface of the quartz oscillator 6 is electrically connected to the terminal 4' on the substrate 1, which faces the terminal 4 thereon in the direction of the diameter thereof, in a minimum area and thickness by using an electrically conducting bonding agent (not shown). This is in order to minimise the forces acting on the chip. In the same manner as in the first embodiment, each of the terminals 4 and 4' is electrically connected to an external terminal placed on the back of the substrate 2 (namely, the surface opposite to the one with the quartz oscillator 2) by using an electrical connection such as a via through the substrate 2. With this configuration, a voltage can be applied from the dry, rear surface of the substrate 1, where the quartz oscillator 6 is not placed, to the detection electrode 3 and the non-detection electrode.

In the second embodiment, the quartz oscillator 6 is also fixed flexibly on the substrate, by bonding the side of the quartz oscillator 6 with the surface of the substrate 1 by using the elastic bonding agent 5. According to this, as in the first embodiment, it is possible to achieve the desired surface-contacting, non-adhesive, distributed support of the oscillation surface of the quartz oscillator 6 onto the surface of the substrate 1.

Figure 6:
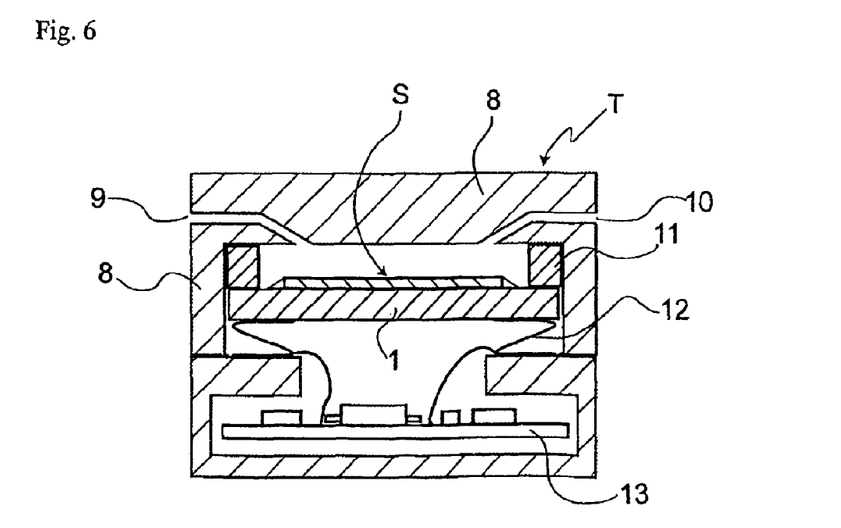
FIG. 6 is a sectional view of a flow-type liquid-phase quartz oscillator sensor in which a chip quartz oscillator in accordance with the present invention is installed.

Several application examples will be described here in regard to the chip quartz oscillator S of the present invention. FIG. 6 is a sectional view showing an example of a flow-type liquid-phase quartz oscillator sensor using a chip quartz oscillator S of the first or second embodiment described by referring to FIGS. 1–5. An inflow entrance 9 and a drain hole 10 are arranged in the vessel 8, to enable a sample solution to enter the vessel and come into contact with the detection electrode of the chip quartz oscillator S inside-the flow-type liquid-phase quartz oscillator sensor T. The substrate of the chip quartz oscillator S is fixed between cushioning material 11, such as an elastic body such as an O-ring or a flexible gasket, and a preferably elastic electric junction 12, such as an elastic metal such as flat spring or dampening pin. The cushioning material 11 is used to preventing the sample solution from flowing into the region around the rear side of the substrate of the chip quartz oscillator S, and the electric junction 12 is used for electrically connecting the terminals of the electrodes placed on the back of the substrate 1 of the chip quartz oscillator S to the circuit board 13 which is conveniently arranged inside the liquid-phase sensor. The circuit board 13 can comprise the circuit layout of the oscillation circuit, together with a quartz oscillator, and appropriate circuit components arranged on the board.

The temperature of the chip quartz oscillator S is preferably kept constant to reduce a source of errors by using an appropriate heating or cooling element such as a Peltier element (not shown).

The mounting forces are directly applied to the quartz oscillator through the elastic body in the prior art. However, as shown in FIG. 6, in the present invention, the chip quartz oscillator S is fixed flexibly in the vessel 8 by using the elastic bodies that are the cushioning material 11 and the electric junction 12. Additionally, the substrate 1 is fixed in the vessel 8, thereby preventing the mounting forces from being applied to the quartz oscillator 2 or 6. In addition to this, even when micro-deformation of the vessel 8 occurs due to minute changes of temperature or flow rate during the operation, such micro-deformations are absorbed by the cushioning material 11 and elastic electric junction 12. Broadening the range of condition where the flow-type liquid-phase quartz oscillator sensor T is usable with high reproducibility, these structural features contribute to the achievement of a liquid sensor with higher reliability.

The cushioning material 11 such as O-ring or gasket is used for convenience of replacing the chip quartz oscillator S, and therefore, it can be substituted with any other functional equivalents, for example, a combination of cushioning material and inner surface of the vessel 8 in one. Similarly, the elastic electric junction 12 is not essential: for example, the electric junction may be omitted, and a flexible contact on the circuit board 13 may be connected directly to a terminal on the back of the substrate 1 of the chip quartz oscillator S. Further, it is preferable to connect a flow tube to either one, or both, of the inflow entrance 9 and the drain hole 10 in the flow-type liquid-phase quartz oscillator sensor T, according to need.

Figure 7:
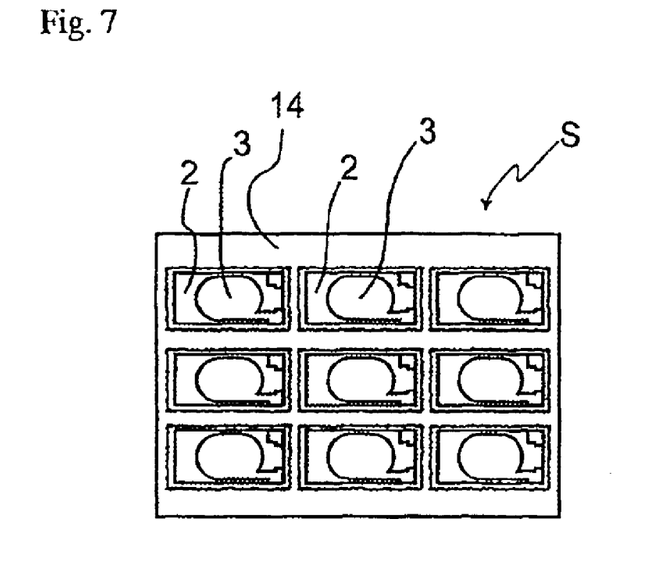
FIG. 7 is a plan view from above of a chip quartz oscillator in which multiple quartz oscillators of the type shown in FIG. 1 are arranged on the same substrate.

FIG. 7 is a plan view from above showing the chip quartz oscillator S in which multiple units of the quartz oscillator 2 of the type shown in FIG. 1 are arranged on a single unit of the substrate 14. This shows a grid-like arrangement on a single substrate 14 of multiple units of the first and second embodiments of the present invention. It is possible to apply power to each of the quartz oscillator 2 or 6 from the single surface, which is opposite to the one with the quartz oscillator 2 or 6, of the substrate 14 in this case as well. Each unit of the quartz oscillator 2 or 6 can independently be bonded to the substrate 14 and connected electrically in the same manner as described previously for the first and second embodiments of the present invention.

In the structure indicated in FIG. 7, not only multiple units of the quartz oscillator 2 or 6 but also multiple units of the electrode 3 are arranged in a matrix, thereby permitting simultaneous detection of different types of targets in a solution in contact with the matrix by arranging a different molecular ligand on each detection electrode. In addition, the chip quartz oscillator can be moved around or replaced by handling a single unit of the substrate 14 alone, and thus it is possible to improve the efficiency of operation for detection. Multiple flow-type liquid-phase quartz oscillator sensors can be used for each purpose, and there is no restriction in respect of the number and the arrangements thereof.

Figure 8:
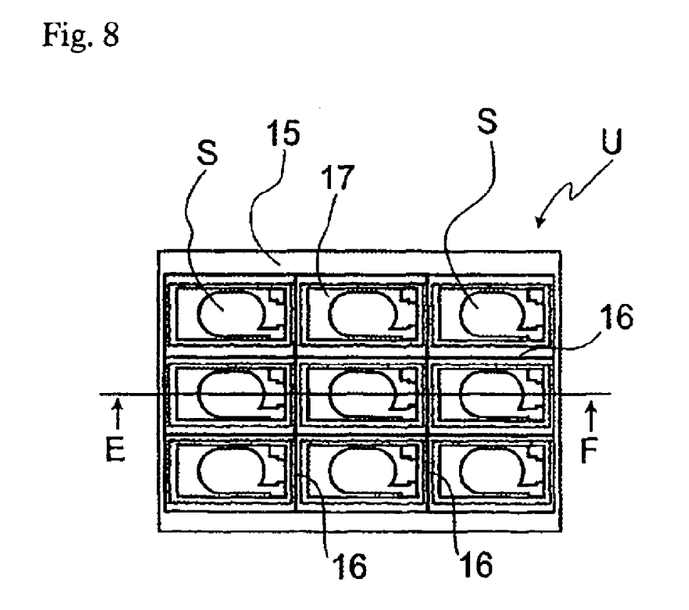
FIG. 8 is a plan view from above of a batch-type liquid-phase quartz oscillator sensor in which a chip quartz oscillator in accordance with the present invention is arranged in each tub-like vessel for containing a sample solution.
Figure 9:
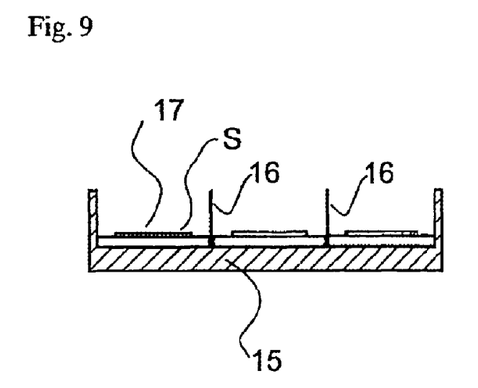
FIG. 9 is a sectional view along the line E–F in FIG. 8.

FIG. 8 is a plan view from above showing an example of a batch-type liquid-phase quartz oscillator sensor U having multiple units of the chip quartz oscillator S of the present invention arranged thereon, and FIG. 9 is a sectional view along the line E-F indicated in FIG. 8. In these figures, a frame 15, which is made of electrical insulating material has an opening on upper side, is partitioned longitudinally and transversely by separators 16, for example in the form of waterproof interconnected walls, to form multiple units of the tub-like vessel 17 arrayed in a lattice therein, and a chip quartz oscillator S in accordance with the first or second embodiment of the present invention is fixed in each tub-like vessel 17. Each tub-like vessel 17 can hold a sample of the sample solution therein, and the detection electrode 3 or 7 of the chip quartz oscillator S placed therein is exposed to the sample solution.

As can be seen from the configuration indicated in FIGS. 8 and 9, in the batch-type liquid-phase quartz oscillator sensor U, a single unit of the chip quartz oscillator S can be placed in every tub-like vessel 17, thereby achieving simultaneous measurement of multiple solutions to be tested as well as improving the efficiency of operation for detection. In addition, each tub-like vessel 17 is isolated from others, and, as a consequence, it is possible to perform detection with only a single unit of the tub-like vessel; thus the batch-type sensor U is useful for samples (for example, samples with high viscosity or containing test substances that are detectable after a period of relatively long reaction time in the detection vessels), which can hardly be detected with the flow-type vessel as shown in FIG. 6.

Multiple batch-type liquid-phase quartz oscillator sensors U can be used for many purposes, and there is no restriction in respect of the number and the arrangement thereof. The shape of the tub-like vessel 17 is not limited to the rectangular shape shown in the figure, and any shapes are acceptable for the vessel in as far as the vessel is capable of keeping the chip quartz oscillator S inside. In addition, any arrangement of the chip quartz oscillator S in the tub-like vessel 17 is acceptable, as far as the detection electrode 3 or 7 thereof is exposed to sample solution and an electrical connection is ensured between the terminal on the back of the substrate 1 and the corresponding circuit in each chip quartz oscillator 12; for example, the chip quartz oscillator S can be installed on a side of the frame 15. Further, it is possible to arrange the chip quartz oscillator S upside down at the boundary between sample solution and the vapour phase thereof so that the detection electrode of the chip quartz oscillator S is placed above, and in contact with, the sample solution. It is also possible to mount the quartz oscillator 2 or 6 on the surface of the bottom part of the frame 15, by omitting the substrate 1 of each chip quartz oscillator S and assuming that the surface on the bottom or side of the frame 15 is equivalent to the substrate 1.

Figure 10:
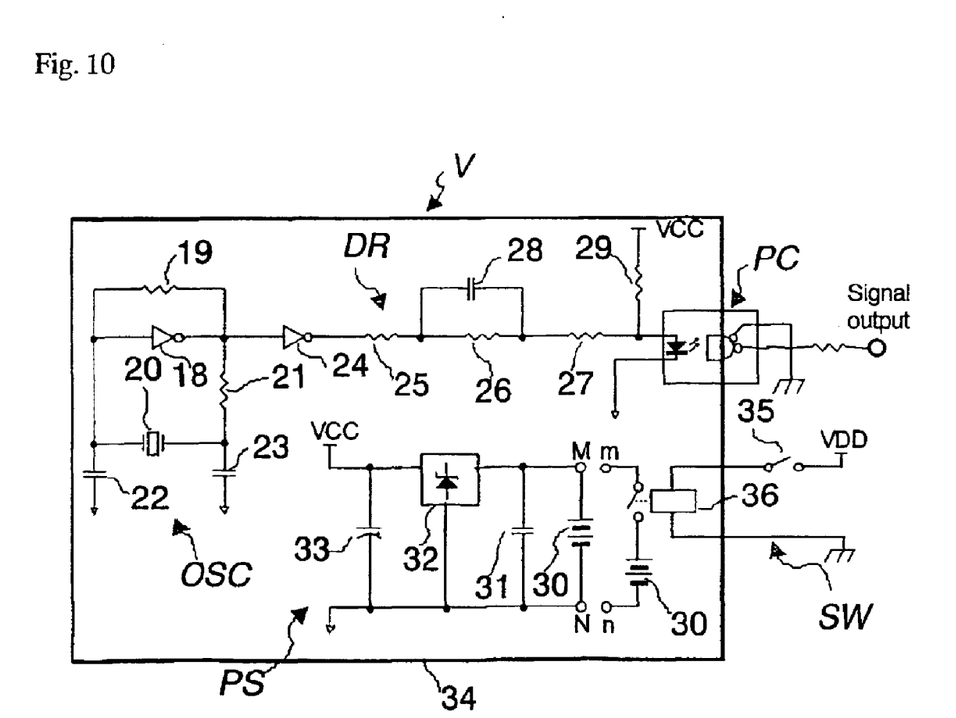
FIG. 10 is a circuit diagram showing the electrical configuration of a quartz oscillation device of the present invention.

FIG. 10 is a circuit diagram schematically showing an example of the configuration of a quartz oscillator device in accordance with the present invention, which contains the above-describe chip quartz oscillator S as a component. As shown in this figure, the quartz oscillator device V has an oscillation circuit section OSC, a photocoupler section PC, a driving section DR and a power source section PS.

The oscillation circuit section OSC consists of an inverter 18, a resistor 19, a chip quartz oscillator 20, a resistor 21, and a capacitors 22 and 23; the inverter 18 constitutes a NOT circuit. The resistor 19, which is connected between the output and input terminals of the inverter 18, is a feedback element. The resistor 21 is an element for limiting the current flowing into the chip quartz oscillator 20, and together with the resistor 21, the chip quartz oscillator 20 is connected between the output and input terminals of the inverter 18. The detection electrode of the chip quartz oscillator 20, which operates as a sensor, is in contact with a sample solution. The capacitor 22 is connected between the detection electrode of the chip quartz oscillator 20 and the ground; the capacitor 23 is connected between the non-detection electrode of the chip quartz oscillator 20 and the ground.

The output of the oscillation circuit section OSC is transmitted to the photocoupler section PC through the driving section DR. The driving section DR consists of an inverter 24, series resistors 25, 26, and 27, and a capacitor 28 that is connected in parallel with the resistor 26; an end of the resistor 27 is connected with a light-emitting element in the photocoupler section PC. The anode of the light-emitting element in the photocoupler section PC is connected through the resistor 29 with the power source voltage VCC. The output of the quartz oscillator device V is outputted from the photoreceptor element in the photocoupler section PC.

In order to reduce mains noise, the power source section PS, which supplies the power source voltage to each component of the quartz oscillator device V, preferably consists of a battery 30, a capacitor 31 that is connected in parallel to the battery 30, a constant-voltage circuit 32, and a capacitor 33 required for connecting the output terminal of the constant-voltage circuit 32 to ground.

Each section constituting the quartz oscillator device V and the means for keeping the chip quartz oscillator in contact with sample solution are preferably installed in the metal vessel 34, thereby electrically shielding each component in the metal vessel 34. The metal vessel 34 is preferably made removable, and, for example, battery replacement can be performed after removing the metal vessel 34. The operability can be improved by substituting the element placed between the terminal M and N of the battery with the element placed between the terminals m and n of the switching circuit SW consisting of the battery 30, a relay 36, an external switch 35 and a driving direct-current power source voltage VDD thereby switching the oscillation circuit section OSC on and off, by installing the external switch 35 outside the metal vessel 34, and by connecting the external switch 35 through the relay 36 with the oscillation circuit section OSC to keep the electrical shield effective.

Thus, the output of the oscillation circuit section OSC is electrically isolated from external devices such as a frequency counter by using the photocoupler section PC, the power source voltage is supplied to each circuit section from the battery 30, and the whole is shielded by installing it in the metal vessel, thereby preventing the fluctuation of oscillation frequency caused by the variation of the power source voltage due to external noises and, as a consequence, achieving a steady oscillation frequency thereof. Furthermore, the configuration shown in FIG. 10 is particularly advantageous and has a prominent effect, when the quartz oscillation device must be isolated electrically from other devices, for example, when multiple quartz oscillators are arranged in a matrix on a substrate as shown in FIG. 7, when multiple electrodes are exposed to a sample solution, or when it is arranged in a place where it can establish an inductive connection with other electrical devices (for example, a temperature controller) through the sample solution or can establish direct electrical continuity to the devices.

A quartz oscillator is usually operated by a direct-current power source of 5 V. It has been recognised that it tends to change its oscillation frequency in response to even small variations in the applied power voltage when its Q decreases markedly such as in the case of immersing it into a liquid phase. For example, the change of 1 mV in applied voltage caused a change of oscillation frequency of about 10 Hz in the case of a 27-MHz AT-cut quartz oscillator. In order to achieve an oscillation frequency output stability in the order of Hz or sub-Hertz, the power source voltage must have a stability in the order of micro-volts. This means that it is not negligible that there are inductive external noises coming into the quartz oscillation device through the wiring and micro-fluctuations of voltage caused by noises originating from external devices such as a power source circuit. However, it is not easy to cancel such micro-fluctuations by using a compensator. By taking these technical backgrounds into consideration, in the quartz oscillation circuit of the present invention, perfect electrical isolation is achieved by installing the battery and other required circuit elements in a shield as well as by designing the configuration where the oscillation output is drawn out through a photocoupler. Thus, with the present invention it is possible to considerably reduce the possibilities of external noises coming in, and to achieve a high stability of oscillation frequency output.

Figure 11:
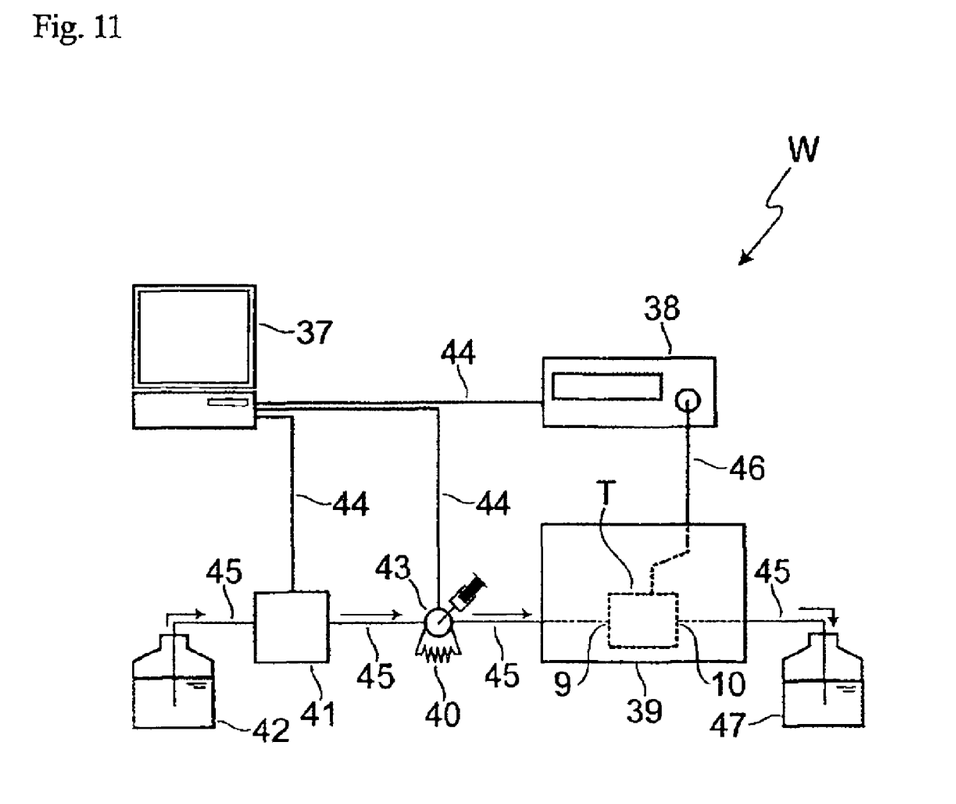
FIG. 11 is a block diagram of a flow-type liquid-phase quartz oscillator sensor device in which a chip quartz oscillator in accordance with the present invention is installed.

FIG. 11 is a schematic diagram showing an example of a configuration for the practical use of a flow-type liquid-phase quartz oscillator sensor T where a chip quartz oscillator S according to the present invention is integrated, which includes peripheral devices. The flow-type liquid-phase quartz oscillator sensor device 39 consists of the flow-type liquid-phase quartz oscillator sensor T, which is described above by referring to FIG. 6, a heating or cooling element such as a Peltier element for keeping the temperature of the sensor constant, and a thermally insulated outer vessel. The electrical shield as described above with reference to FIG. 10 is achieved by using a metal vessel capable of electrical insulation as the outer vessel for the flow-type liquid-phase quartz oscillator sensor device 39 or by enclosing the flow-type liquid-phase quartz oscillator sensor T with another metal vessel as shown in FIG. 11. The sample solution, after being placed in the vessel for supplying sample solution 42, is allowed to flow through the flow tube 45 by using the pump 41, which is capable of providing a constant flow rate without a pulsating flow, and the solution goes through the valve with injector 43 and is supplied from the inflow entrance 9 to the flow-type liquid-phase quartz oscillator sensor T; the solution is discharged through the drain hole 10 to the waste liquid container 47. There is a possibility that the detection electrode 3 of the chip quartz oscillator S becomes conductive to the outside through the sample solution when the flow tube 45 is removed from the flow-type liquid-phase quartz oscillator sensor device 39 and, as a result, the electrical shielding by the metal vessel fails to work. However, usually, the effective resistance of sample solution is relatively large, and the conducting effect is negligible in practice and the shielding effect is ensured when a non-conducting plastic tube with small inner and outer diameters (e.g. an outer diameter of about 1 mm and inner diameter of 0.25 mm or less) is used as the flow tube 45.

A solution containing substances to be tested can be injected to the tube for test solution 40 through the valve with injector 43 by using an injection syringe, and then the solution can be supplied to the flow-type liquid-phase quartz oscillator sensor T by turning the switch of the valve with injector 43. The output oscillation frequency of the flow-type liquid-phase quartz oscillator sensor T can be transmitted through a coaxial cable 46 to a frequency counter 38, measured by the counter 38 at fixed intervals or continuously, and then transmitted by an interface such as GPIB or RS232C through a communication cable 44 to a computer 37. The computer 37 with the interface such as GPIB or RS232C preferably is made capable of controlling the pump 41 and the valve with injector 43 through a communication cable 44. The procedure of performing the measurement comprises the steps of: applying power to the flow-type liquid-phase quartz oscillator sensor device 39 to initiate the oscillation; actuating the thermo-controller of the liquid-phase quartz oscillator sensor 39; simultaneously allowing a liquid to flow at a constant rate with the pump 41; and turning the valve with injector 43 and allowing a sample solution to flow into the flow-type liquid-phase quartz oscillator sensor T when the output oscillation frequency becomes steady in the flow-type liquid-phase quartz oscillator sensor T. The output oscillation frequency changes in proportion to the minute change in mass caused by sample adsorption on and release from the detection electrode 3 of the chip quartz oscillator S. The change can be measured in the frequency counter and the data can be captured and recorded in the computer 37 at fixed intervals and/or continually. The examples described below were measured by using this system configuration, the flow-type liquid-phase quartz oscillator sensor device and the peripheral device W.

Figure 12:
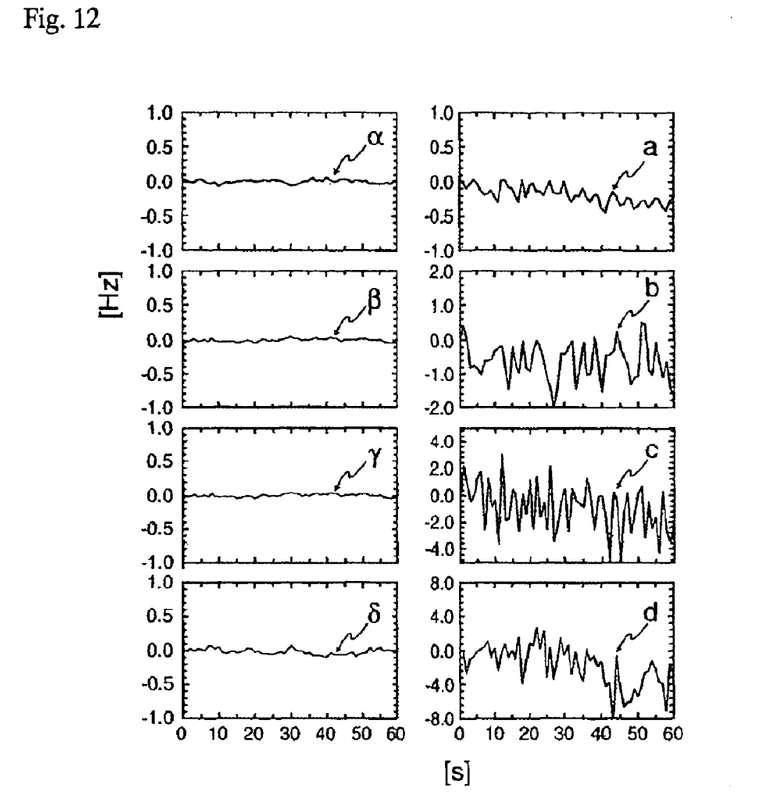
FIG. 12 is a graph showing an experimental result of the stability in output signal depending on flow rate in the flow-type liquid-phase quartz oscillator sensor comparing the chip quartz oscillator of the present invention against the previous-type chip quartz oscillator supported with O-ring.

FIG. 12 shows an experimental result of the stability of output signal against the flow rate of a sample solution; a prior art-type quartz oscillator directly supported with O-rings as indicated in FIGS. 14 and 15 was installed in the flow-type liquid-phase quartz oscillator sensor indicated in FIG. 16, and a chip quartz oscillator S in accordance with the present invention indicated in FIGS. 1 and 2 was installed in the flow-type liquid-phase quartz oscillator sensor T; the results obtained by the two types of sensors are compared with each other in this figure. In each case, the quartz oscillator is placed at the position of the quartz oscillator 20 indicated in FIG. 10. The ordinate indicates the relative oscillation frequency of the quartz oscillation device as designed above; the abscissa indicates time. Pure water was used as a sample solution, i.e. no solution containing a substance to be tested was injected, and therefore, no adsorption-and-release phenomenon occurred on the electrode during the measurement. Accordingly, during the experiment, changes in oscillation frequency are understood not to be derived from mass change.

In FIG. 12, curves, a, b, c, and d represent output frequency response in the flow-type liquid-phase quartz oscillator sensor using the previous-type direct-support with O-ring, and curves, α, β, γ, and δ represent output frequency response in the flow-type liquid-phase quartz oscillator sensor T with a chip quartz oscillator S in accordance with the present invention. The flow rate of sample solution was 0 µl/minute in curves a and α; 10 µl/minute in curves b and β; 50 µl/minute in curves c and γ; 100 µl/minute in curves d and δ.

The curves, a–d in FIG. 12 indicates that fluctuation of the frequency increases with increases in the flow rate in the case of the previous-type quartz oscillator directly supported with O-ring. This is because the quartz oscillator directly supported by O-rings is easily distorted by the fluid pressure of the sample solution. However, as indicated by the curves, α–δ, the inventive chip quartz oscillator S is hardly affected by increases in fluid pressure and as a result fluctuations of the oscillation frequency are very small.

Figure 13:
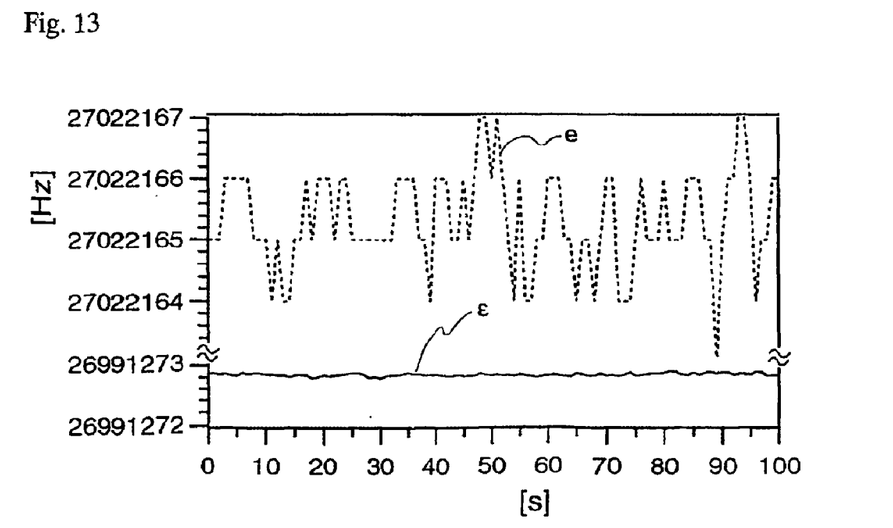
FIG. 13 is a graph showing an experimental result of the stability in oscillation frequency output, comparing a quartz oscillation device in accordance with the present invention and an ordinary quartz oscillation device operated from an AC power source.

FIG. 13 is a graph showing an experimental result, where stability in output oscillation frequency obtained by the quartz oscillator device V shown in FIG. 10 is compared with that obtained by an ordinary quartz oscillation device operated with AC power source. The ordinate indicates frequency (Hz); the abscissa indicates time (second). The measurement was performed by using the flow-type liquid-phase quartz oscillator sensor T with the inventive chip quartz oscillator S indicated in FIG. 6. Like in the example described above, pure water was used as a sample solution and no solution containing a substance to be tested was injected. In the ordinary quartz oscillation device operated with AC power source, power is supplied to the quartz oscillator by rectifying and dropping down the voltage from the commercial AC line (at e.g. 100 volts), and the oscillation output is directly connected to the frequency counter. Thus, as seen from curve e, output frequency of the ordinary quartz oscillation device operated with AC power source varies considerably depending on external noises coming through the wiring as well as noises from the power source circuit. However, as seen from curve ε, in the quartz oscillation device V indicated in FIG. 10, output of the oscillation device is connected through a photocoupler to an external device, the power is supplied from a battery, and the whole oscillation device is enclosed and shielded with a metal vessel, thereby electrically insulating the device from external devices; thus fluctuations of oscillation frequency, which are due to noises in the power source circuit, are extremely small and steady oscillation can be achieved.

As understood from the above description of the several embodiments and application examples, in the present invention, the side-wall of a quartz oscillator is designed to be flexibly attached to the surface of the substrate, while the surface of the oscillator facing the surface of the substrate is not attached to the surface of the substrate, thereby achieving surface-contacting, non-adhesive, distributed support of the quartz oscillator by the substrate. This design has the extraordinary effect that the quartz oscillator is hardly distorted even when having deformation stresses caused by change in property of sample solution in contact with the quartz oscillator or caused by device operation such as flow of sample solution, and as a result steady oscillation is achieved. In addition, it has the merit to protect the quartz oscillator against mechanical damages since the quartz oscillator can be moved around or replaced without handling it directly as it can be handled by gripping the substrate.

It has also the great advantage to ensure the steady operation of the oscillation device; even when multiple quartz oscillators operate simultaneously while being immersed in a conducting fluid, electrical interference such as short circuits is not generated between the quartz oscillation devices each of which contain a quartz oscillator, because each quartz oscillator is fixed on one side of the substrate and a circuit component electrically connected to the quartz oscillator is placed on the other side of the substrate.

Furthermore, according to the present invention, all the electrical components required for the quartz oscillation device can be insulated electrically and isolated from other electrical components, because the quartz oscillation circuit with the chip quartz oscillator, together with the power source section required for the circuit is designed to be installed and shielded electrically in a metal vessel. Additionally, the output from the oscillation circuit is designed to be connected through a photocoupler to an external device. Accordingly, this removes fluctuations of oscillation frequency caused by changes in the power source voltage due to external noises, thereby ensuring the steady oscillation of the liquid-phase sensor and further improving the effective sensitivity of the liquid-phase sensor.

Figure 17:
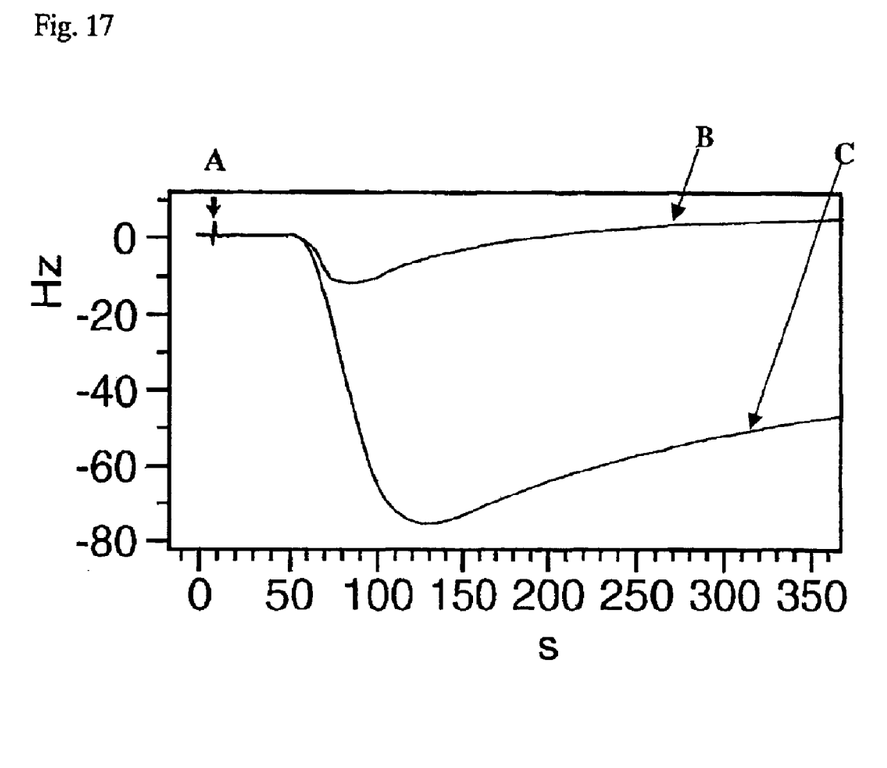
FIG. 17 is a graph showing an experimental result in which is shown a change in oscillation frequency due to molecules binding to a chip quartz oscillator in accordance with the present invention.

FIG. 17 shows a graph displaying experimental results obtained from chip quartz oscillators in accordance with the present invention used for the specific detection of a protein-protein interaction. The x-axis of the graph displays time in seconds and the y-axis shows the change in oscillation frequency of the oscillators. Two chip quartz oscillators, each with a nominal oscillation frequency of 27 MHz, were used in this experiment. The first oscillator was prepared with a mouse anti-myoglobin (Biacore) pre-immobilized sensor surface constructed through a self-assembled monolayer of 3,3'-dithiodipropionic acid deposited on its gold detection electrode while the second oscillator was prepared with a bovine serum albumin (BSA, Amersham Pharmacia Biotech)-pre-immobilized sensor surface constructed through a self-assembled monolayer of 3,3'-dithiodipropionic acid deposited on its gold detection electrode.

A sample of 50 µl of 5.0 µg/ml (0.30 µM) sheep myoglobin (MW. 16,923, Biacore) solution was injected onto each oscillator using 50 mM HEPES buffer (pH 7.4) with 0.2 M NaCl as a running buffer. The flow rate was 100 µl/min and the operating temperature was 25.00° C.

Upon the injection of myoglobin solution at time A, the chip quartz oscillator having a myoglobin-pre-immobilised surface responded to yield a relatively large decrement of the frequency (curve C), showing that myoglobin had become bound to its detection electrode and demonstrating that a specific protein-protein interaction can be measured by an appropriately prepared sensor. The oscillator with the non-specific surface (BSA-pre-immobilised surface) only showed a low response to the analyte (curve B) and this was mainly due to a minute change in the density of the buffer upon the injection of the solute. This illustrates that a chip quartz oscillator in accordance with the present invention may be used to detect the presence of specific molecules present in a liquid which is in contact with the detection electrode of the chip quartz oscillator.

The above mentioned embodiments are intended to illustrate the present invention and are not intended to limit the scope of protection claimed by the following claims.

EXPLANATION OF REFERENCE NUMERALS

1: substrate, 1': upper surface of substrate, 2: rectangular quartz oscillator, 2': first surface, 2": second surface, 2'": side-wall 3: detection electrode, 3': lead electrode, 3" non-detection electrode, 3'": lead electrode 4: terminal, 4': terminal, 5: elastic bonding agent, 6: circulat quartz oscillator, 6': first surface, 6": second surface, 6'": side-wall, 7: detection electrode, 7': lead electrode, 8: vessel, 9: inflow entrance, 10: drain hole, 11: cushioning material, 12: electric junction, 13: circuit board, 14: substrate, 15: frame, 16: separator, 17: tub-like vessel, 18: inverter, 19: resistor, 20: chip quartz oscillator, 21: resistor, 22: capacitor, 23: capacitor, 24: inverter, 25: resistor, 26: resistor, 27: resistor, 28: capacitor, 29: resistor, 30: battery, 31: capacitor, 32: constant-voltage circuit, 33: capacitor, 34: metal vessel, 35: external switch, 36: relay, 37: computer, 38: frequency counter, 39: flow-type liquid-phase quartz oscillator sensor device, 40: tube for test solution, 41: pump, 42: vessel for supplying sample solution, 43: valve with injector, 44: communication cable, 45: flow tube, 46: coaxial cable, 47: waste liquid container, 48: quartz oscillator, 49: O-ring or gasket, 50: vessel, 51: inflow entrance, 52: drain hole, 53: circuit board, S: chip quartz oscillator, T: flow-type liquid-phase quartz oscillator sensor, W: flow-type liquid-phase quartz oscillator sensor device and peripheral devices, U: batch-type liquid-phase quartz oscillator sensor, V: quartz oscillation device, OSC: oscillation circuit section, PC: photocoupler section, DR: driving section, PS: power source section, SW: switching circuit.

What is claimed is:

1. A chip quartz oscillator comprising a plurality of quartz of oscillators (2; 6), each having a first surface (2'; 6') and a second surface (2"; 6") joined by a side-wall (2'"; 6'"), wherein each quartz oscillator further has a detection electrode (3; 7) on said first surface (2'; 6') and a non-detection electrode (3", 7") on said second surface (2"; 6") and wherein each quartz oscillator (2; 6) is flexibly mounted on a substrate (14), and further wherein the surface (2"; 6") of said quartz oscillator (S) facing towards said substrate (1; 14) is in contact with said substrate (1; 14) but does not adhere to said substrate (1; 14).

2. A chip quartz oscillator comprising a plurality of quartz of oscillators (2; 6), each having a first surface (2'; 6') and a second surface (2"; 6") joined by a side-wall (2'"; 6'"), wherein each quartz oscillator further has a detection electrode (3; 7) on said first surface (2'; 6') and a non-detection electrode (3", 7") on said second surface (2"; 6") and wherein each quartz oscillator (2; 6) is flexibly mounted on a substrate (14), and further comprising at least a quartz oscillation circuit section (OSC) for causing said quartz oscillator to oscillate and to output a signal relating to the oscillation frequency of said quartz oscillator;

a photocoupler section (PC) for transmitting the output from the quartz oscillation circuit section to an external device, a power source section (PS) containing a battery for supplying voltage to the quartz oscillation circuit section (OSC) and the photocoupler section (PC), and a shield for insulating the quartz oscillation circuit section, the photocoupler section, and the power source section in order to prevent fluctuation of oscillation frequency caused by external noises.

* * * * *